United States Patent
Jia

(10) Patent No.: US 6,270,562 B1
(45) Date of Patent: Aug. 7, 2001

(54) FILLER MATERIAL FOR DENTAL COMPOSITES

(75) Inventor: Weitao Jia, Wallingford, CT (US)

(73) Assignee: Jeneric/Pentron, Inc., Wallingford, CT (US)

(*) Notice: Subject to any disclaimer, the term of this patent is extended or adjusted under 35 U.S.C. 154(b) by 0 days.

(21) Appl. No.: 09/329,725

(22) Filed: Jun. 10, 1999

Related U.S. Application Data

(60) Provisional application No. 60/088,920, filed on Jun. 11, 1998.

(51) Int. Cl.$^7$ ............................... C08K 7/00; C08K 3/40; B32B 7/00
(52) U.S. Cl. .................. 106/35; 106/400; 106/485; 428/372; 428/378; 428/300.1; 523/115; 523/200; 523/202; 523/216; 523/217; 523/220; 523/221; 433/201.1; 433/212.1; 433/222.1; 433/223
(58) Field of Search ................... 428/372, 378, 428/300.1; 106/35, 400, 485; 523/115, 200, 202, 216, 217, 220, 221; 433/201.1, 212.1, 222.1, 223

(56) References Cited

U.S. PATENT DOCUMENTS

| | | | |
|---|---|---|---|
| 2,477,268 | 7/1949 | Saffir | 32/2 |
| 2,514,076 | 7/1950 | Kelly | 18/55.1 |
| 3,066,112 | 11/1962 | Bowen | 260/41 |
| 3,179,623 | 4/1965 | Bowen | 260/47 |
| 3,194,784 | 7/1965 | Bowen | 260/41 |
| 3,312,569 * | 4/1967 | Philipps et al. | 117/126 |
| 3,751,399 | 8/1973 | Lee, Jr. et al. | 260/17 |
| 3,923,740 | 12/1975 | Schmitt et al. | 260/47 |
| 3,926,906 | 12/1975 | Lee, II et al. | 260/42.53 |
| 4,381,918 | 5/1983 | Ehrnford | 433/199 |
| 4,392,828 | 7/1983 | Ehrnford | 433/217 |
| 4,544,359 | 10/1985 | Waknine | 523/115 |
| 4,547,531 | 10/1985 | Waknine | 523/116 |
| 4,894,012 | 1/1990 | Goldberg et al. | 433/215 |
| 4,894,102 * | 1/1990 | Halls et al. | 156/94 |
| 5,276,068 | 1/1994 | Waknine | 522/28 |
| 5,444,104 | 8/1995 | Waknine | 522/24 |
| 5,541,238 * | 7/1996 | Yamada et al. | 523/200 |
| 5,621,035 | 4/1997 | Lyles et al. | 524/404 |
| 5,707,440 | 1/1998 | Hengchang et al. | 106/485 |
| 5,707,734 * | 1/1998 | Hawkins et al. | 428/372 |
| 5,861,445 * | 1/1999 | Xu et al. | 106/35 |
| 5,969,000 | 10/1999 | Yang et al. | 523/116 |
| 6,013,694 | 1/2000 | Jia et al. | 523/116 |

OTHER PUBLICATIONS

Rosenstiel SF; Gupta PK; Van Der Sluys RA; Zimmerman MH; "Strength of a Dental Glass–Ceramic After Surface Coating", Dental Materials, 1993, 9(4) :274–279, Jul.

Suchanek, W; Yashima M; Kakihana M; "Processing and Mechanical Properties of Hydroxyapatite Reinforced with Hydroxyapatite Whiskers", Biomaterials, 1996, 17(17) :1715–1723 Sep.

Xu HH; Martin TA; Antonucci JM: Eichmiller FC; "Ceramic Whisker Reinforcement of Dental Resin Composites", Journal of Dental Research, 1999, 78(2) :706–712, Feb.

\* cited by examiner

Primary Examiner—C. Melissa Koslow
(74) Attorney, Agent, or Firm—Ann M. Knab

(57) ABSTRACT

A filler material comprising a fibrous material and one or more forms of surface-modifying particles for use in dental composites and dental restorations. The surface-modifying particles are bonded to the fibrous material to increase the surface area of the fibrous material and improve the bonding properties of the fibrous material to enable it to better bond to a resin matrix material in a dental composite. In accordance with the present invention, the fibrous material possesses a lower melting temperature than the surface-modifying particles. The surface-modifying particles and the fibrous material are heated to a temperature below the softening temperature of the fibrous material but at a temperature and time sufficient to soften the surface of the fibrous material in order to bond the surface-modifying particles thereto.

33 Claims, 3 Drawing Sheets

FILLER MATERIAL FOR DENTAL COMPOSITES

This application claims priority of Provisional Application Ser. No. 60/088,920 filed on Jun. 11, 1998 which is hereby incorporated by reference.

TECHNICAL FIELD

The present invention relates generally to filler materials and methods of manufacture thereof and more specifically to filler materials for use in dental composite materials.

BACKGROUND OF THE INVENTION

Compositions useful for repairing damaged teeth in situ are known in the art as direct filling materials, and include alloys and resin composites. Dental amalgam alloys have widely been used as direct filling material, and provide excellent handling characteristics, and physical properties. The technique of mechanically packing and condensing a material into a tooth cavity is previously known to the dental profession in connection with the use of dental amalgams as a direct filling material. It has well known advantages in that it permits a close adaptation of the filling material to the cavity walls and also makes it possible to make firm contacts between the restored tooth and its neighbor. Further, it makes it possible to give the restoration its final anatomic form before hardening, thereby avoiding the time consuming and difficult finishing work with rotating instruments required with composite materials. However, there are perceived health hazard concerns regarding the use of high amounts of mercury or gallium present in amalgam alloys.

Dental resins have accordingly been developed, which comprise polymeric matrices, for example polyamides, polyesters, acrylates, polyolefins, polyimides, polyarylates, polyurethanes, vinyl esters, or epoxy-based materials. Other polymeric matrices include styrenes, styrene acrylonitriles, ABS polymers, polysulfones, polyacetals, polycarbonates, polyphenylene sulfides, and the like. The most popular polymeric matrices are based on monomers having at least one ethylenically unsaturated group, in particular acrylate and methacrylate groups. One commonly used monomer of this class is the reaction product of bisphenol A with glycidyl methacrylate (hereinafter BIS-GMA). In addition, these resins have also been used to make artificial teeth and denture bases.

Unfilled (i.e., pure) curable acrylic and methacrylic resins generally suffer from polymerization shrinkage and poor durability. These drawbacks have been reduced in direct filling applications, in part, through the addition of inert fillers. See, for example, U.S. Pat. No. 3,066,112 which is herein incorporated by reference. The combination of binder plus filler is commonly referred to as a composite direct filling material. Currently used fillers for curable dental resins generally are inert materials in the form of finely divided irregular particles, fibers or beads, present in an amount from about 35 to about 80 percent by weight of the total composite direct filling material.

Commonly used inorganic fillers include fumed silica, quartz, glass, various mineral silicates (e.g., B-eucryptite, lepidolite, petalite, spondumene, beryl, topaz and zircon), silicon carbide, alumina, and mixtures thereof Commonly-assigned U.S. Pat. No. 4,544,359 to Waknine, for example, discloses a filler mixture comprising barium silicate, borosilicate glass, and colloidal silica. In general composite direct filling materials which are fully loaded with inorganic fillers (i.e. combined with the highest workable volume loading) having particles in the range of 0.01–1.2 microns are the most wear-resistant currently available composite direct filling materials. However, these composite direct filling materials containing finely divided inorganic fillers and acrylic binder resins may not polish as easily as unfilled dental resin.

U.S. Pat. No. 5,707,440 to Hengchang et al. is directed to finely divided inorganic filler comprising macro-filler particles and micro-filler particles. Each macro-filler particle has a number of micro-filler particles covering it and connected to it by sintering. In addition to mixing and sintering the macro-filler and micro-filler particles together, the method of making the filler mixture requires dispersing the resultant mixture in a liquid and using ultrasonic waves to separate the coarser particles to settle from the dispersion, and centrifuging the dispersion to claim the finely divided inorganic filler. A commercial product comprising filler based on this technology is available from Heraeus Kulzer GmbH under the name Solitare.

Organic materials have also been used as fillers. For example, U.S. Pat. No. 3,923,740 discloses a direct filling material containing finely divided cured polymethyl methacrylate, alone or in conjunction with an inorganic filler. Composite direct filling materials which are wholly or partly filled with finely divided polymethyl methacrylate have better polishability (i.e. better surface finish after polishing with ordinary dental tools) than composite direct filling materials which are fully loaded with inorganic fillers, but generally have poorer durability (i.e. poorer wear resistance in vivo) than composite direct filling materials having inorganic fillers only.

Regarding fibrous fillers in particular, U.S. Pat. No. 2,477,268 to Saffir discloses short glass fibers randomly dispersed in dental resin materials, as does U.S. Pat. No. 2,514,076 to Kelly. Use of long, fully wetted fibers in structural components for dental restorations and the like are disclosed in U.S. Pat. No. 4,894,102 to Goldberg et al. However, none of these patents discloses a composite having the feel of amalgam.

Fused-fibrous filler compositions in the dental arts are also known. Such fused fibrous fillers are of particular interest because they reportedly provide a feel similar to that of amalgam when used by the dentist, and may be applied using similar techniques. In U.S. Pat. Nos. 4,381,918 and No. 4,392,828 to Ehlnford there is disclosed a filler comprising porous inorganic particles which are completely or partially impregnated with a resin material. The porous inorganic particles are formed by heating inorganic fibers under pressure to fuse the fibers at their points of contact, thereby forming a rigid three-dimensional network of inorganic fibers. Fused-fibrous filler compositions are also disclosed in U.S. Pat. No. 5,621,035 to Lyles et al. Such fillers comprise silica fibers together with either alumina or aluminosilicate fibers which are fused in the presence of a fusion source such as boron nitride. The presence of boron lowers the melting point of the fibers sufficiently to allow formation of a porous, interconnected network. The network is then ground to particles having a size of about 180 microns, and used as fillers in dental composites. Unfortunately, use of the aforementioned fused-fibrous filler compositions requires multiple steps and extensive preparation time.

Accordingly, there is a need in the dental arts to develop a dental resin composite which is similar to or approaching dental amalgam alloys in handling characteristics, physical properties, and applications without the drawbacks and deficiencies associated with dental amalgam alloys, and without the multiple preparation steps required for fused-fibrous compositions.

SUMMARY OF THE INVENTION

These and other objects and advantages are accomplished by the composition and method of manufacture of the present invention directed to a filler material comprising a fibrous material and one or more forms of surface-modifying particles. The surface-modifying particles are bonded to the fibrous material to increase the surface area of the fibrous material and improve the bonding properties of the fibrous material to enable it to better bond to a resin matrix material in a dental composite. In accordance with the present invention, the fibrous material possesses a lower melting temperature than the surface-modifying particles. The surface-modifying particles and the fibrous material are heated to a temperature below the softening temperature of the fibrous material but at a temperature and time sufficient to soften the surface of the fibrous material in order to chemically bond the surface-modifying particles thereto.

The resulting filler material can be used in dental composites and dental restorations to provide optimal handling properties, good wear resistance and high strength.

BRIEF DESCRIPTION OF THE DRAWINGS

Features of the present invention are disclosed in the accompanying drawings, wherein similar reference characters denote similar elements throughout the several views, and wherein.

DETAILED DESCRIPTION OF THE INVENTION

Figure 1:
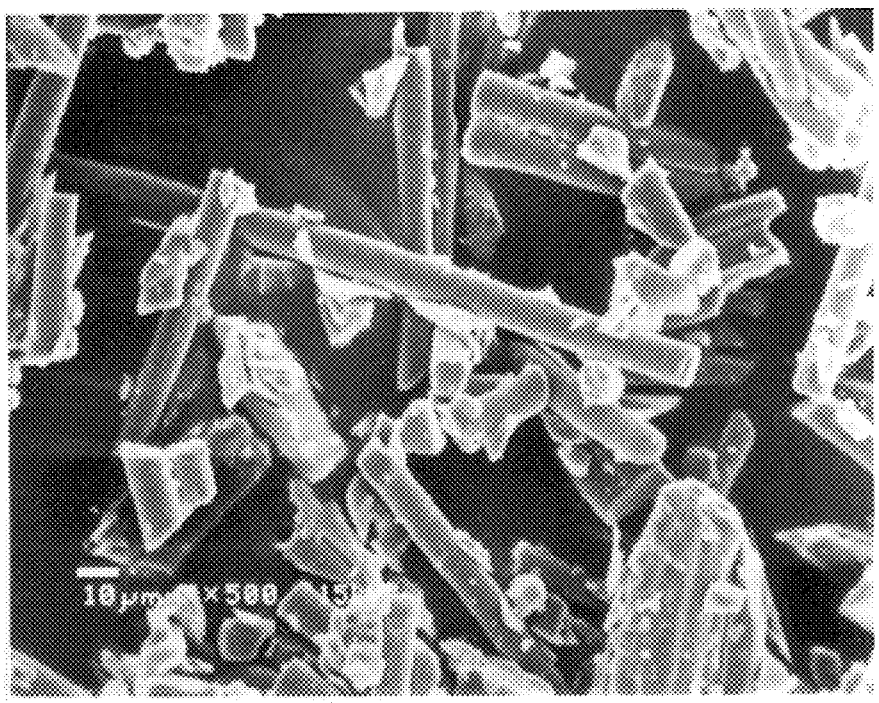
FIG. 1 is a photomicrograph of filler material comprising solely fibrous material.

The present invention is directed to a filler material that can be used to form dental composites and restorations in accordance with known procedures. The filler material of the present invention comprises a mixture of a fibrous material and one or more forms of surface-modifying particles. The surface-modifying particles are bonded to the fibrous material to increase its surface area and to improve the bonding properties of the fibrous material to enable it to better bond to a resin matrix material in a dental composite. Dental composite materials having good physical properties are realized using the filler material of the present invention. Dental composites using the filler material of the present invention exhibit flexural strengths equal to or greater than about 105 MPa, a flexural modulus equal to or greater than about 15 GPa and a Vickers hardness equal to or greater than about 965 MPa.

A number of fibrous materials are suitable for use in the practice of the present invention, including but not being limited to ceramic and known fibrous glass materials listed in Table 1 below. A preferred fibrous material is comprised of S-2 GLASS®, which is commercially available from Owens Corning. The fibers used in the present invention can be any standard size and preferably are below about 15 microns in diameter and more preferably are below about 10 microns in diameter. The length of the fibers can be any standard length, preferably less than or equal to 1/16 inch. The fibrous material may include glass fibers, ceramic fibers or both glass and ceramic fibers.

TABLE 1

| Oxide* | A-Glass | C-Glass | D-Glass | E-Glass | ECR-Glass ® | AR-Glass | R-Glass | S-2 Glass ® |
|---|---|---|---|---|---|---|---|---|
| SiO$_2$ | 63–72 | 64–68 | 72–75 | 52–56 | 54–62 | 55–75 | 55–65 | 64–66 |
| Al$_2$O$_3$ | 0–6 | 3–5 | 0–1 | 12–16 | 9–15 | 0–5 | 15–30 | 24–25 |
| B$_2$O$_3$ | 0–6 | 4–6 | 21–24 | 5–10 | | 0–8 | | |
| CaO | 6–10 | 11–15 | 0–1 | 16–25 | 17–25 | 1–10 | 9–25 | 0–0.1 |
| MgO | 0–4 | 2–4 | | 0–5 | 0–4 | | 3–8 | 9.5–10 |
| ZnO | | | | | 2–5 | | | |
| BaO | | 0–1 | | | | | | |
| Li$_2$O | | | | | | 0–1.5 | | |
| Na$_2$O + K$_2$O | 14–16 | 7–10 | 0–4 | 0–2 | 0–2 | 11–21 | 0–1 | 0–0.2 |
| TiO$_2$ | 0–0.6 | | | 0–1.5 | 0–4 | 0–12 | | |
| ZrO$_2$ | | | | | | 1–18 | | |
| Fe$_2$O$_3$ | 0–0.5 | 0–0.8 | 0–0.3 | 0–0.8 | 0–0.8 | 0–5 | | 0–0.1 |
| F$_2$ | 0–0.4 | | | 0–1 | | 0–5 | 0–0.3 | |
| Softening point, ° C. | 705 | 750 | 771 | 846 | 882 | 773 | 952 | 1056 |

*Percent by weight

The surface-modifying particles, in general, can include any suitable filler material such as those set forth in commonly assigned U.S. Pat. Nos. 5,444,104, 4,547,531 and 4,544,359 all to Waknine, which are incorporated by reference herein. The surface modifying particles can include filler material which is capable of being covalently bonded to the resin matrix itself or to a coupling agent such as γ-methacryloxy propyltrimethoxysilane which is available from OSi Specialties, Inc., Friendly, WV under the name Silquest A-174 which is covalently bonded to both the filler and the resin. Suitable filling materials materials include, but are not limited to, silica, silicate glass, quartz, barium silicate, strontium silicate, borosilicate, barium borosilicate, strontium borosilicate, lithium silicate, amorphous silica, ammoniated or deammoniated calcium phosphate, alumina, zirconia, tin oxide, titania, aluminum nitride, silicon nitride, titanium nitride, aluminum carbide, silicon carbide and titanium carbide. Preferred surface-modifying particles are those listed in Table 2 below. The particle size of the surface-modifying particles is preferably but not limited to the range of about 0.001 to about 5.0 microns depending upon the type of filler used, and more preferably is in the range of about 0.01 to about 1.0 micron. Preferably, the surface-modifying particles are smaller than the fibers such that the surface-modifying particles attach along the surface of the fibers.

TABLE 2

| Oxide* | GM 32087 | GM 27884 | 8235 | GM 31685 | GM 31684 |
|---|---|---|---|---|---|
| $SiO_2$ | 50 | 55 | 50 | 60 | 50 |
| $Al_2O_3$ | 15 | 10 | 10 | 20 | 20 |
| $B_2O_3$ | 15 | 10 | 10 | — | — |
| MgO | — | — | — | 5 | — |
| ZnO | — | — | — | 1 | 1 |
| BaO | 1 | 25 | 30 | — | — |
| $Li_2O$ | — | — | — | 5 | 5 |
| SrO | 20 | — | — | — | — |
| $K_2O$ | — | — | — | 1 | 1 |
| $ZrO_2$ | — | — | — | 5 | 5 |
| $Ta_2O_3$ | — | — | — | 1 | 1 |
| $La_2O_3$ | — | — | — | — | 10 |
| $P_2O_5$ | — | — | — | — | 5 |
| ZnO | 0–0.4 | — | — | 1 | 1 |
| Transformation Temp. ° C. | 680 | 665 | 630 | >800 | >800 |

*Percent by weight

FIG. 1 illustrates filler material comprising solely S-2 GLASS® fibers. The fibers appear to have a smooth, clean surface. FIGS. 2 through 5 illustrate filler material manufactured in accordance with the present invention comprising fibers and surface-modifying particles. The fibers appear to have a rough surface as a result of the surface-modifying particles bonded thereto.

In the practice of the present invention, the filler material can be manufactured by mixing together, using any known mixing method, the fibrous material and the surface-modifying particles. Preferably, the fibrous material has a lower melting temperature than the surface-modifying particles. The fibrous material is mixed with the surface-modifying material in a conventional manner such as, for example, ball milling in a solvent such as an ethanol solvent to obtain a homogeneous mixture. The ratio of fibrous material to surface-modifying material is preferably about 1 part by weight fibrous material to about 0.5 to about 5 parts by weight surface-modifying material. After the mixing step, the mixture is dried typically at room temperature, thereby removing the solvent, and heated below the softening temperature of the fibrous material for a time effective to soften the surface of the fibrous material. The surface of the fibrous material softens to the point of being able to bond to the surface-modifying particles. Such temperature and time are interdependent, and are empirically determined, based on the composition (and thus the softening point) of the fibrous material. Higher temperatures will generally result in shorter times. The temperature must be high enough to soften the surface of the fibrous material, but not so high as to cause extensive fusion of the fibers or melting of the surface-modifying particles. The temperature of heat treatment is in preferably in the range of about 700° C. to about 1200° C. and more preferably in the range of about 800° C. to about 1000° C.

The resultant filler material may be ground to the desired particle size suitable for use as a filler in a dental restoration, preferably below about 100 microns and more preferably below about 80 microns. As used herein, grinding refers to any known methods for size reduction, including reduction to spherical or fiber form. To obtain the desired amalgam "feel", the particles are ground to a size of less than about 60 microns. At this size, the particles generally retain a fibrous form, that is, a length greater than their diameter. The resultant filler may further be etched and/or treated with a coupling agent such as a silane compound which is known in the art to provide coupling between materials.

The polymeric matrix portion of the dental composite is selected from those known in the art of dental materials, including those listed in commonly assigned U.S. patent application Ser. No. 08/951,414, filed Oct. 16, 1997, now U.S. Pat. No. 6,013,694, which is incorporated by reference herein. The polymeric matrix materials include but are not limited to expandable monomers, liquid crystal monomers, ring-opening monomers, polyamides, acrylates, polyesters, polyolefins, polymides, polyarylates, polyurethanes, vinyl esters or epoxy-based materials. Other polymeric matrices include styrenes, styrene acrylonitriles, ABS polymers, polysulfones, polyacetals, polycarbonates, polyphenylene sulfides, and the like. These polymeric matrices are derived from curing polymeric matrix precursor compositions Such precursor compositions are well-known in the art, and may be formulated as one-part, two-part, or other compositions, depending on the components.

Preferred materials include those based on acrylic and methacrylic monomers, for example those disclosed in U.S. Pat. Nos. 3,066,112, 3,179,623, and 3,194,784 to Bowen; U.S. Pat. Nos. 3,751,399 and 3,926,906 to Lee et al.; and commonly assigned U.S. Pat. No. 5,276,068 to Waknine and application Ser. No. 08/998,849 filed on Dec. 29, 1997, now U.S. Pat. No. 5,969,000 all of which are herein incorporated by reference in their entirety. Especially preferred methacrylate monomers include the condensation product of bisphenol A and glycidyl methacrylate, 2,2'-bis [4-(3-methacryloxy-2-hydroxy propoxy)-phenyl] propane (hereinafter abbreviated BIS-GMA), the condensation product of ethoxylated bisphenol A and glycidyl methacrylate, (hereinafter EBPA-DMA), and the condensation product of 2 parts hydroxymethylmethacrylate and 1 part triethylene glycol bis(chloroformate) (hereinafter PCDMA). Polyurethane dimethacrylates (hereinafter abbreviated to PUDMA) are also commonly-used principal polymers suitable for use in the present invention.

The polymeric matrix precursor composition may further comprise a co-polymerizable diluent monomer. Such monomers are generally used to adjust the viscosity of the polymerizable composition, which affects wettability of the composition. Suitable diluent monomers include, without limitation, hydroxyalkyl methacrylates, such as 2-hydroxyethyl methacrylate, 1,6-hexanediol dimethacrylate, and 2-hydroxypropyl methacrylate; glyceryl dimethacrylate; ethyleneglycol methacrylates, including ethyleneglycol methacrylate, diethyleneglycol dimethacrylate, triethyleneglycol dimethacrylate and tetraethyleneglycol dimethacrylate; or diisocyanates, such as 1,6-hexamethylene diisocyanate. Triethyleneglycol dimethacrylate (TEGDMA) is particularly preferred for use in the present invention.

The polymeric matrix precursor composition typically includes polymerization initiators, polymerization accelerators, ultra-violet light absorbers, anti-oxidants, fluorescent whitening agents, and other additives well known in the art. The polymer matrices may be visible light curing, self-curing, dual curing, and vacuum-, heat-, and pressure-curable compositions as well as any combination thereof Visible light curable compositions employ light-sensitive compounds such as benzil diketones, and in particular, dl-camphorquinone in amounts ranging from about 0.05 to 0.5 weight percent. UV absorbers are particularly desirable in the visible light curable compositions in order to avoid discoloration of the resin form any incident ultraviolet light. Suitable UV absorbers are the various benzophenones, particularly UV-9 and UV-5411 available from American Cyanamid Company, and benzotriazoles known in the art, particularly 2-(2'-hydroxy-5'-methylphenyl)benzotriazole, sold under the trademark TINUVIN P by Ciba-Geigy Corporation, Ardsley, N.Y. in amounts ranging from about 0.05 to about 5.0 weight percent.

In the self-curing compositions, a polymerization accelerator may be included in the polymerizable monomer composition. The polymerization accelerators suitable for use include the various organic tertiary amines well known in the art, generally aromatic tertiary amines, such as dimethyl-p-toluidine, dihydroxyethyl-p-toluidine and the like, in amounts ranging from about 0.05 to about 4.0 weight percent, and generally acrylate derivatives such as dimethylaminoethyl methacrylate and particularly, diethylaminoethyl methacrylate in amounts ranging from about 0.05 to 0.5 weight percent.

The heat and pressure curable compositions include, in addition to the monomeric components, a heat cure initiator such as benzoyl peroxide, 1,1'-azobis (cyclohexanecarbonitrile), or other suitable free radical initiators. Particularly suitable free radical initiators are lauroyl peroxide, tributyl hydroperoxide, AIBN and, more particularly benzoyl peroxide or 1,1'-azobis (cyclohexanecarbonitrile).

The total amount of filler is determined by the specific function of the filled materials, being in the range from about 5 to 95% by weight of the total composite composition. Preferably, the composites of the present invention may also include additional inorganic and/or organic fillers or a mixtures thereof currently used in dental restorative materials. Additional fillers may include one or more of silica, silicate glass, quartz, barium silicate, strontium silicate, barium borosilicate, borosilicate, lithium silicate, amorphous silica, ammoniated or deammoniated calcium phosphate, alumina, zirconia, tin oxide and titania. Preferably, the additional filler is barium borosilicate in an amount between about 5% and about 85% by weight of the total composite composition. Examples of glass fillers include a composition having about 55 % Sir, 10% $Al_2O_3$, 25% BaO, and 10% $B_2O_3$ and a composition having about 50 % $SiO_2$, 10% $Al_2O_3$, 30% BaO, and 10% $B_2O_3$. When used as a direct filling material, the desired amalgam "feel" is obtained by using about 10 to about 60 % by weight of filler comprising fibers and surface-modifying particles and from about 30 to about 80% by weight of other filler, for example barium borosilicate. A preferred composition comprises about 18% by weight of a resin mixture comprising EBP-DMA and PCDMA in a ratio of 70:30 by weight, about 40% by weight of ground, fibrous/surface-modifying particles filler and 42% by weight of barium borosilicate filler.

The following examples illustrate the practice of the invention.

EXAMPLE 1

Figure 2:
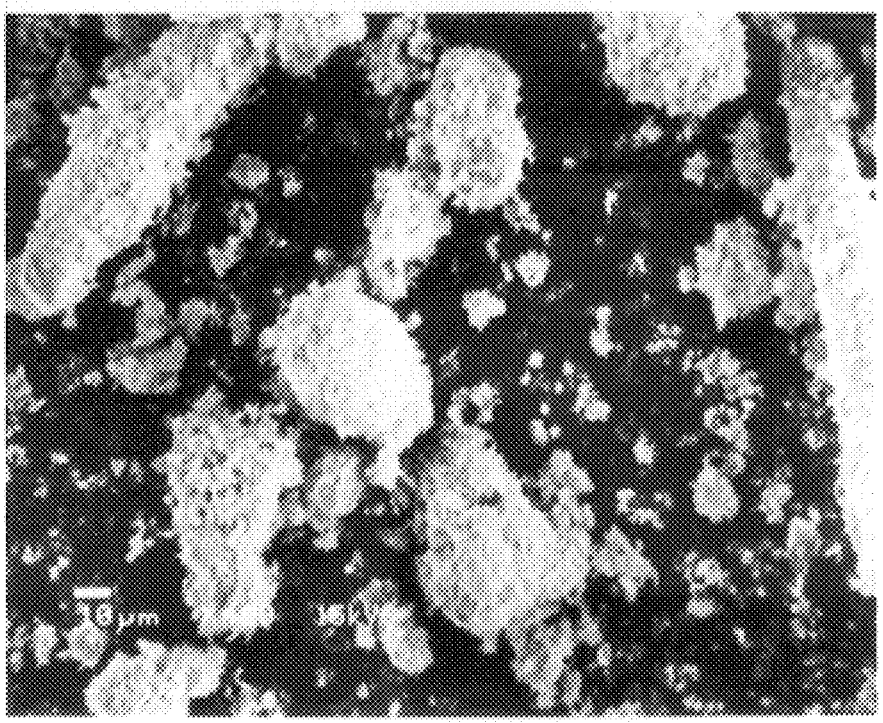
FIG. 2 is a photomicrograph of filler material processed in accordance with the present invention comprising fibrous material and two different forms of surface-modifying particles.

1 part by weight of E-GLASS fibers, available from Owens-Corning, having an average length of about 1/32 inch and an average diameter of about 8–10 microns, 1.5 parts by weight of Schott glass filler, available from Schott Glaswerke, Landshut, Germany under product number GM32087, having a particle size of 0.7 microns and 0.5 parts by weight of fumed silica, available from Degussa Corporation, Ridgefield, N.J. under the name Aerosil OX-50, are mixed in a ball mill in the presence of a water/ethanol solvent for about two hours. The ratio of fibers to surface-modifying particles is 1:2. The mixture is dried at room temperature and then heated at 780° C. for two hours. The resultant product is then crushed and ground to a particle size of about 60 microns. FIG. 2 shows the microstructure of the resultant filler material. The glass filler and fumed silica are shown bonded to the surface of the E-GLASS fibers.

EXAMPLE 2

Figure 3:
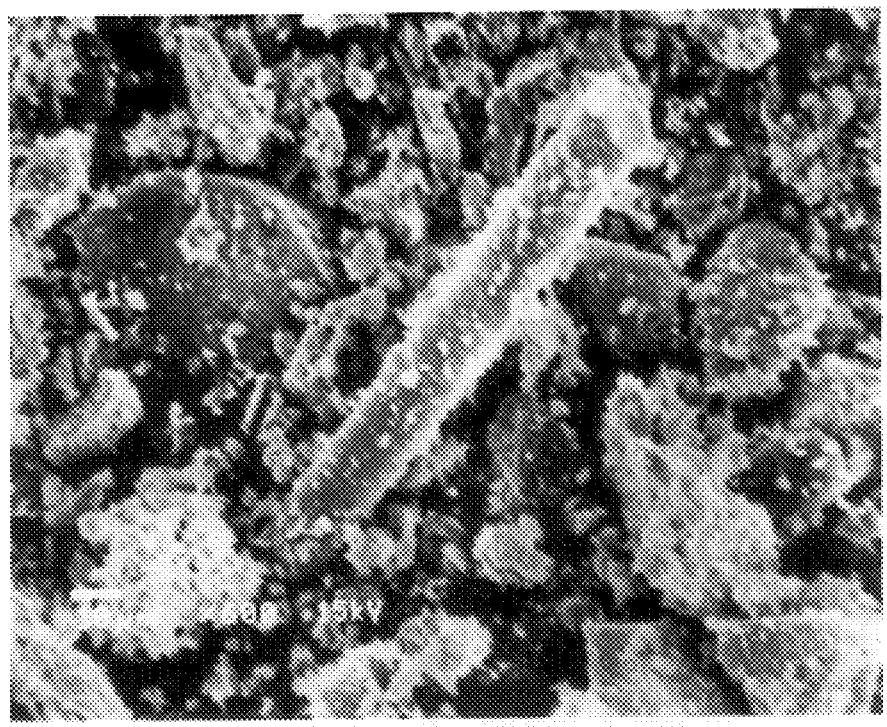
FIG. 3 is a photomicrograph of filler material processed in accordance with the present invention comprising fibrous material and one form of surface-modifying particles.

1 part by weight of E-GLASS fibers is mixed with 5 parts by weight of Schott glass filler, available from Schott Glaswerke, Landshut, Germany under product number GM32087, having a particle size of 0.7 microns, in a ball mill in the presence of a water/ethanol solvent for two hours. The mixture is dried at room temperature and then heated at 780° C. for one hour. The resultant product is then crushed with a mortar and pestle. FIG. 3 shows the microstructure of the resultant filler material. The glass filler is shown bonded to the surface of the E-GLASS fibers.

EXAMPLE 3

Figure 4:
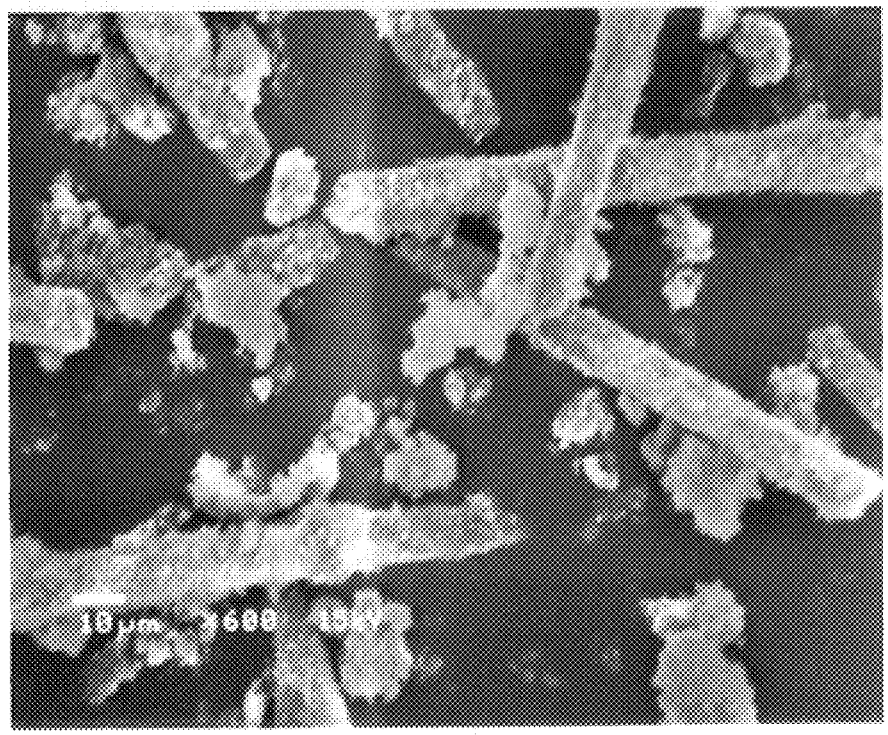
FIG. 4 is a photomicrograph of filler material processed in accordance with the present invention comprising fibrous material and a different form of surface-modifying particles from used in the filler shown in FIG. 3.

1 part by weight of S-2 GLASS® fibers having an average length of 1/16 inch is mixed with 1.5 parts by weight of Aerosil OX-50 fined silica in a ball mill in the presence of a water/ethanol solvent for three hours. The mixture is dried at room temperature and then heated at 960° C. for three hours. The resultant product is then crushed with a mortar and pestle. FIG. 4 shows the microstructure of the resultant filler material. The fumed silica is shown bonded to the surface of the S-2 GLASS® fibers.

EXAMPLE 4

Figure 5:
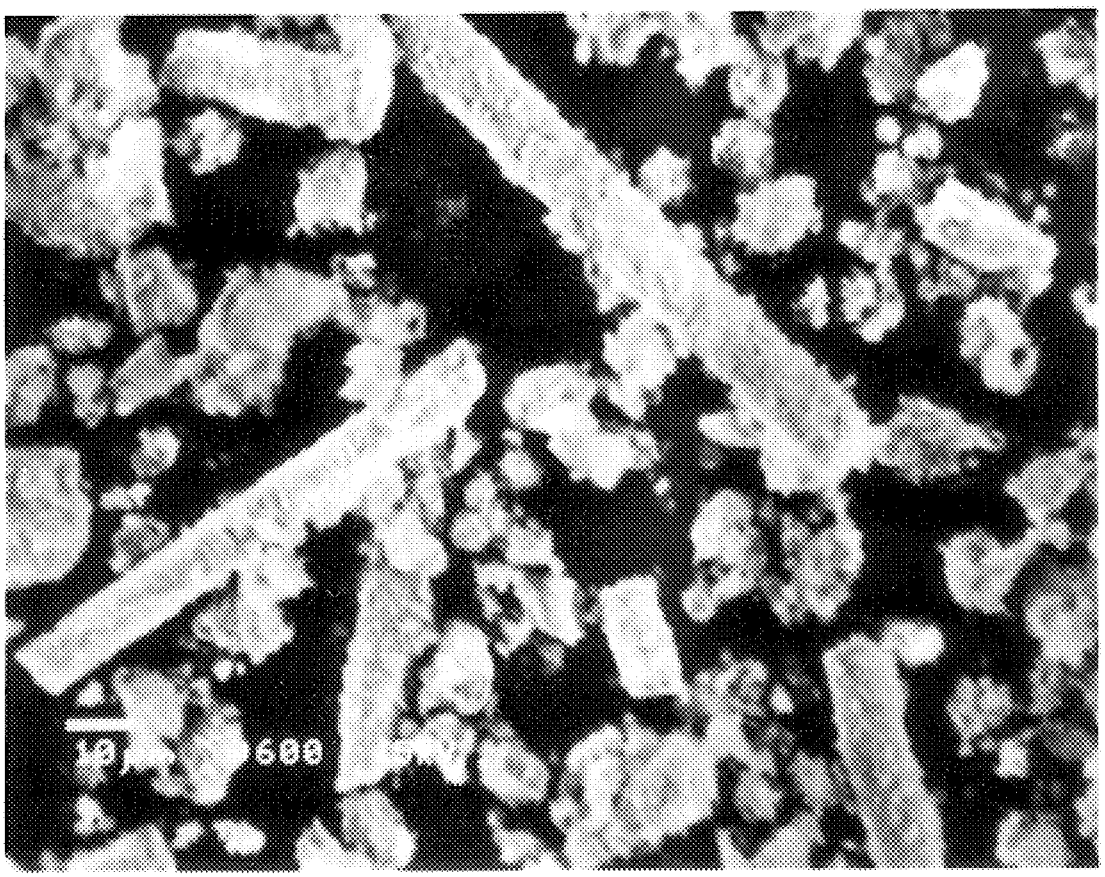
FIG. 5 is a photomicrograph of filler material processed in accordance with the present invention comprising fibrous material and one form of surface-modifying particles and processed at a temperature different from that used in making the filler shown in FIG. 4.

1.5 parts by weight of S-2 GLASS® fibers are mixed with 1 part by weight of Aerosil OX-50 fumed silica in a ball mill in the presence of a water/ethanol solvent for three hours. The mixture is dried at room temperature and then heated at 980° C. for two hours. The resultant product is then crushed with a mortar and pestle. FIG. 5 shows the microstructure of the resultant filler material. The fumed silica is shown bonded to the surface of the S-2 GLASS® fibers.

EXAMPLE 5

1.5 parts by weight of S-2 GLASS® fibers is mixed with 1 part by weight of Aerosil OX-50 fumed silica and processed according to the steps set forth in Example 4 above except that the heating temperature is 1000° C. Thirty nine percent (39%) of the resultant filler is then mixed with forty three point nine percent (43.9%) of GM 27 884 Schott glass filler. The filler mixture is then mixed with seventeen point 1 percent (17.1%) resin mixture comprising EBP-DMA and PCDMA in a ratio of 70:30 by weight. The composite is cured and tested for physical properties. The properties are set forth in Table 2.

EXAMPLE 6

Filler material obtained from Example 4 is mixed in an amount of 41.5% with 41.1% of 8235 Schott glass filler. The filler mixture is then mixed with 17.4% resin mixture comprising EBP-DMA and PCDMA in a ratio of 70:30 by weight. The composite is cured and tested for physical properties. The properties are set forth in Table 2.

EXAMPLE 7

Filler material obtained from Example 4 is mixed in an amount of 41.7% with 41.25% of GM 27 884 Schott glass filler used in Example 1. The filler mixture is then mixed with 17.05% resin mixture comprising EBP-DMA and PCDMA in a ratio of 70:30 by weight. The composite is cured and tested for physical properties. The properties are set forth in Table 3.

TABLE 3

|  | Flexural Strength MPa (S.D.) | Flexural Modulus GPa (S.D.) | Vickers Hardness MPa (S.D.) |
| --- | --- | --- | --- |
| Example 5 | 105 (12.4) | 15.9 (1.5) | 1039 (57) |
| Example 6 | 111 (8.4) | 15.7 (1.2) | 965 (18) |
| Example 7 | 110 (5.4) | 15.1 (1.5) | 985 (28) |
| (Comparison) Solitaire* | 53 (8.7) | 2.5 (0.2) | 480 (20) |

*Available from Heraeus Kulzer GmbH, Germany

As will be appreciated, the present invention provides a filler composition having high strength and good bonding properties particularly useful in the fabrication of dental restorations.

While various descriptions of the present invention are described above, it should be understood that the various features can be used singly or in any combination thereof Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A filler material for dental composites comprising:
a fibrous material, and
surface-modifying particles;
wherein the surface-modifying particles are bonded to the fibrous material;
wherein the surface-modifying particles are fabricated of a glass; and
wherein the glass has a composition comprising about 50% $SiO_2$, 15% $Al_2O_3$, 1% BaO, 20% SrO, and 15% $B_2O_3$.

2. The filler of material of claim 1 wherein the fibrous material is fabricated of glass or ceramic fibers.

3. A filler material for dental composites comprising:
a fibrous material; and
surface-modifying particles;
wherein the surface-modifying particles are bonded to the fibrous material;
wherein the fibrous material comprises a plurality of glass fibers; and
wherein the glass fibers have a composition comprising about 64–66% $SiO_2$, 24–25% $Al_2O_3$, 0–0.1% CaO, 9.5–10% MgO, 0–0.2% $Na_2O+K_2O$, and 0–0.1% $Fe_2O_3$.

4. The filler material of claim 3 wherein the surface-modifying particles are fabricated of at least one of silica, silicate, ammoniated or deammoniated calcium phosphate, alumina, zirconia, tin oxide, titania, aluminum nitride, silicon nitride, titanium nitride, aluminum carbide, silicon carbide and titanium carbide.

5. A filler material for dental composites comprising:
a fibrous material; and
surface-modifying particles;
wherein the surface-modifying particles are bonded to the fibrous material;
wherein the fibrous material comprises a plurality of glass fibers; and
wherein the glass fibers have a composition comprising about 52–56% $SiO_2$, 12–16% $Al_2O_3$, 5–10% $B_2O_3$, 16–25% CaO, 0–5% MgO, 0–2% $Na_2O+K_2O$, 0–1.5% $TiO_2$, 0–0.1% $Fe_2O_3$ and 0–1% $F_2$.

6. The filler material of claim 5 wherein the surface-modifying particles are fabricated of at least one of silica, silicate, ammoniated or deammoniated calcium phosphate, alumina, zirconia, tin oxide, titania, aluminum nitride, silicon nitride, titanium nitride, aluminum carbide, silicon carbide and titanium carbide.

7. A dental composite composition comprising:
filler material, wherein the filler material comprises a fibrous material and surface modifying particles and wherein the surface-modifying particles are bonded to the fibrous material; and
a polymeric matrix precursor composition;
wherein the surface-modifying particles are a glass; and
wherein the glass has a composition comprising about 50% $SiO_2$, 15% $Al_2O_3$, 1% BaO, 20% SrO, and 15% $B_2O_3$.

8. The dental composite composition of claim 7 wherein the fibrous material is fabricated of glass or ceramic fibers.

9. A dental composite composition comprising:
filler material, wherein the filler material comprises a fibrous material and surface modifying particles and wherein the surface-modifying particles are bonded to the fibrous material; and
a polymeric matrix precursor composition;
at least one additional filler material; and
wherein the at least one additional filler material is barium borosilicate present in an amount between about 5% to about 85% by weight of the total composite composition.

10. The dental composite of claim 9 wherein the fibrous material is fabricated of glass or ceramic fibers.

11. The dental composite of claim 9 wherein the surface-modifying particles are fabricated of a at least one of silica, silicate, ammoniated or deammoniated calcium phosphate, alumina, zirconia, tin oxide, titania, aluminum nitride, silicon nitride, titanium nitride, aluminum carbide, silicon carbide and titanium carbide.

12. A dental composite composition comprising:
filler material, wherein the filler material comprises a fibrous material and surface modifying particles and wherein the surface-modifying particles are bonded to the fibrous material;
a polymeric matrix precursor composition; and
at least one additional filler material;
wherein the additional filler is a glass having the composition comprising about 55% $SiO_2$, 10% $Al_2O_3$, 25% BaO, and 10% $B_2O_3$.

13. The dental composite of claim 12 wherein the fibrous material is fabricated of glass or ceramic fibers.

14. The dental composite of claim 12 wherein the surface-modifying particles are fabricated of a at least one of silica, silicate, ammoniated or deammoniated calcium phosphate, alumina, zirconia, tin oxide, titania, aluminum nitride, silicon nitride, titanium nitride, aluminum carbide, silicon carbide and titanium carbide.

15. A dental composite composition comprising:
  filler material, wherein the filler material comprises a fibrous material and surface modifying particles and wherein the surface-modifying particles are bonded to the fibrous material; and
  a polymeric matrix precursor composition;
  at least one additional filler material; and
  wherein the additional filler is a glass having the composition comprising about 50% $SiO_2$, 10% $Al_2O_3$, 30% BaO, and 10% $B_2O_3$.

16. A dental restoration comprising:
  filler material, wherein the filler material comprises a fibrous material and surface modifying particles and wherein the surface-modifying particles are bonded to the fibrous material; and
  a cured polymeric matrix precursor composition;
  wherein the fibrous material comprises a plurality of glass fibers; and
  wherein the glass fibers have a composition comprising about 64–66% $SiO_2$, 24–25% $Al_2O_3$, 0–0.1% CaO, 9.5–10% MgO, 0–0.2% $Na_2O+K_2O$, and 0–0.1% $Fe_2O_3$.

17. The dental restoration of claim 16 wherein the surface-modifying particles are fabricated of a at least one of silica, silicate, ammoniated or deammoniated calcium phosphate, alumina, zirconia, tin oxide, titania, aluminum nitride, silicon nitride, titanium nitride, aluminum carbide, silicon carbide and titanium carbide.

18. A dental restoration comprising:
  filler material, wherein the filler material comprises a fibrous material and surface modifying particles and wherein the surface-modifying particles are bonded to the fibrous material, and
  a cured polymeric matrix precursor composition;
  wherein the fibrous material comprises a plurality of glass fibers; and
  wherein the glass fibers have a composition comprising about 52–56% $SiO_2$, 12–16% $Al_2O_3$, 5–10% $B_2O_3$, 16–25% CaO, 0–5% MgO, 0–2% $Na_2O+K_2O$, 0–1.5% $TiO_2$, 0–0.1% $Fe_2O_3$ and 0–1% $F_2$.

19. The dental restoration of claim 18 wherein the surface-modifying particles are fabricated of a at least one of silica, silicate, ammoniated or deammoniated calcium phosphate, alumina, zirconia, tin oxide, titania, aluminum nitride, silicon nitride, titanium nitride, aluminum carbide, silicon carbide and titanium carbide.

20. A dental restoration comprising:
  filler material, wherein the filler material comprises a fibrous material and surface modifying particles and wherein the surface-modifying particles are bonded to the fibrous material; and
  a cured polymeric matrix precursor composition;
  wherein the surface-modifying particles are a glass; and
  wherein the glass has a composition comprising about 50% $SiO_2$, 15% $Al_2O_3$, 1% BaO, 20% SrO, and 15% $B_2O_3$.

21. A dental restoration comprising:
  filler material, wherein the filler material comprises a fibrous material and surface modifying particles and wherein the surface-modifying particles are bonded to the fibrous material;
  a cured polymeric matrix precursor composition; and
  at least one additional filler material;
  wherein the at least one additional filler material is barium borosilicate present in an amount of about 5% to about 85% by weight of the total composition.

22. A dental restoration comprising:
  filler material, wherein the filler material comprises a fibrous material and surface modifying particles and wherein the surface-modifying particles are bonded to the fibrous material;
  a cured polymeric matrix precursor composition; and
  at least one additional filler material;
  wherein the additional filler is a glass having the composition comprising about 55% $SiO_2$, 10% $Al_2O_3$, 25% BaO, and 10% $B_2O_3$.

23. A dental restoration comprising:
  filler material, wherein the filler material comprises a fibrous material and surface modifying particles and wherein the surface-modifying particles are bonded to the fibrous material;
  a cured polymeric matrix precursor composition; and
  at least one additional filler material;
  wherein the additional filler is a glass having the composition comprising about 50% $SiO_2$, 10% $Al_2O_3$, 30% BaO, and 10% $B_2O_3$.

24. A method of making a dental composite comprising:
  making a filler material comprising mixing fibrous material and surface-modifying particles together to produce an intimate mixture thereof;
  heating the mixture to a temperature and time sufficient enough to create a chemical bond between the surface-modifying particles and the fibrous material to form a filler material;
  wherein the temperature is below the softening temperature of the fibrous material but high enough to soften a surface of the fibrous material to bond the surface-modifying particles thereto, but not so high as to melt the surface modifying particles;
  grinding the filler material to a desired particle size; and
  incorporating the filler material into a polymeric matrix precursor composition to form a dental composite.

25. The method of claim 24 wherein the fibrous material is fabricated of glass or ceramic fibers.

26. The method of claim 25 wherein the glass fibers have a composition comprising about 64–66% $SiO_2$, 24–25% $Al_2O_3$, 0–0.1% CaO, 9.5–10% MgO, 0–0.2% $Na_2O+K_2O$, and 0–0.1% $Fe_2O_3$.

27. The method of claim 25 wherein the glass fibers have a composition comprising about 52–56% $SiO_2$, 12–16% $Al_2O_3$, 5–10% $B_2O_3$, 16–25% CaO, 0–5% MgO, 0–2% $Na_2O+K_2O$, 0–1.5% $TiO_2$, 0–0.1% $Fe_2O_3$ and 0–1% $F_2$.

28. The method of claim 24 wherein the surface-modifying particles are fabricated of at least one of silica, silicate, ammoniated or deammoniated calcium phosphate, alumina, zirconia, tin oxide, titania, aluminum nitride, silicon nitride, titanium nitride, aluminum carbide, silicon carbide and titanium carbide.

29. The method of claim 28 wherein the silica comprises quartz or amorphous silica.

30. The method of claim 28 wherein the silicate comprises barium silicate, strontium silicate, borosilicate, lithium silicate, or silicate glass.

31. The method of claim 30 wherein the borosilicate comprises barium borosilicate.

32. The method of claim 24 wherein the surface-modifying particles are fabricated of a glass, fumed silica or both.

33. The method of claim 24 wherein the glass has a composition comprising about 50% $SiO_2$, 15% $Al_2O_3$, 1% BaO, 20% SrO, and 15% $B_2O_3$.

* * * * *